(12) United States Patent
Ostrovsky et al.

(10) Patent No.: US 9,113,991 B2
(45) Date of Patent: Aug. 25, 2015

(54) ANCHORS FOR BODILY IMPLANTS AND METHODS FOR ANCHORING BODILY IMPLANTS INTO A PATIENT'S BODY

(75) Inventors: Isaac Ostrovsky, Wellesley, MA (US); Jozef Slanda, Milford, MA (US); James Goddard, Pepperell, MA (US); Ken Flynn, Woburn, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 25 days.

(21) Appl. No.: 13/463,503

(22) Filed: May 3, 2012

(65) Prior Publication Data

US 2012/0289980 A1    Nov. 15, 2012

Related U.S. Application Data

(60) Provisional application No. 61/485,388, filed on May 12, 2011.

(51) Int. Cl.
*A61B 17/04* (2006.01)
*A61F 2/00* (2006.01)

(52) U.S. Cl.
CPC ........ *A61F 2/0045* (2013.01); *A61F 2210/0004* (2013.01); *A61F 2220/0008* (2013.01)

(58) Field of Classification Search
CPC ... A61F 2/0045; A61F 2/0063; A61F 2/0811; A61F 2220/0008; A61B 17/0401; A61B 2017/00805; A61B 2017/0409; A61B 17/0487
USPC ........................ 606/139–151, 232; 600/29, 30
See application file for complete search history.

(56) References Cited

U.S. PATENT DOCUMENTS

| | | | |
|---|---|---|---|
| 3,003,155 A | 10/1961 | Mielzynski et al. |
| 5,013,136 A | 5/1991 | Whitehead et al. |
| 5,112,344 A | 5/1992 | Petros |
| 5,197,983 A | 3/1993 | Berman et al. |
| 5,250,054 A | 10/1993 | Li |

(Continued)

FOREIGN PATENT DOCUMENTS

| | | |
|---|---|---|
| AU | 4092199 A | 12/1999 |
| CA | 2333121 A1 | 11/1999 |

(Continued)

OTHER PUBLICATIONS

Search Report and Written Opinion for International Application No. PCT/US2012/036944, mailed Aug. 21, 2012, 12 pages.

(Continued)

*Primary Examiner* — Katherine M Shi
(74) *Attorney, Agent, or Firm* — Brake Hughes Bellermann LLP

(57) ABSTRACT

An anchor is provided for anchoring a bodily implant within a body of a patient. The anchor includes an implant engaging portion for engaging the bodily implant, wherein the implant engaging portion is disposed on a lateral portion of the anchor. The anchor further includes a distal end portion configured to pass through a passageway in the patient's body, the passageway defining a first axis and a proximal end portion disposed longitudinally opposite to the distal end portion on the anchor. The anchor defines a second axis extending from the distal end portion to the proximal end portion. The anchor is configured to rotate when a force is applied to the bodily implant such that the second axis defined by the anchor forms an angle with the first axis defined by the passageway.

19 Claims, 15 Drawing Sheets

(56) References Cited

U.S. PATENT DOCUMENTS

| | | |
|---|---|---|
| 5,425,740 A | 6/1995 | Hutchinson, Jr. |
| 5,439,470 A | 8/1995 | Li |
| 5,439,474 A | 8/1995 | Li |
| 5,443,472 A | 8/1995 | Li |
| 5,449,366 A | 9/1995 | Li |
| 5,464,189 A | 11/1995 | Li |
| 5,500,000 A | 3/1996 | Feagin et al. |
| 5,520,703 A | 5/1996 | Essig et al. |
| 5,549,636 A | 8/1996 | Li |
| 5,575,805 A | 11/1996 | Li |
| 5,611,515 A | 3/1997 | Benderev et al. |
| 5,643,266 A | 7/1997 | Li |
| 5,645,589 A | 7/1997 | Li |
| 5,649,937 A | 7/1997 | Bito et al. |
| 5,690,649 A | 11/1997 | Li |
| 5,697,931 A | 12/1997 | Thompson |
| 5,702,215 A | 12/1997 | Li |
| 5,707,395 A | 1/1998 | Li |
| 5,715,942 A | 2/1998 | Li et al. |
| 5,741,300 A | 4/1998 | Li |
| 5,776,147 A | 7/1998 | Dolendo |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chalfringeon et al. |
| 5,922,026 A | 7/1999 | Chin |
| 5,935,138 A | 8/1999 | McJames, II et al. |
| 5,954,057 A | 9/1999 | Li |
| 6,022,373 A | 2/2000 | Li |
| 6,039,686 A | 3/2000 | Kovac |
| 6,039,761 A | 3/2000 | Li et al. |
| 6,042,534 A | 3/2000 | Gellman et al. |
| 6,042,582 A | 3/2000 | Ray |
| 6,042,592 A | 3/2000 | Schmitt |
| 6,096,060 A | 8/2000 | Fitts et al. |
| 6,099,538 A | 8/2000 | Moses et al. |
| 6,110,101 A | 8/2000 | Tihon et al. |
| 6,117,161 A | 9/2000 | Li et al. |
| 6,129,762 A | 10/2000 | Li |
| 6,149,669 A | 11/2000 | Li |
| 6,200,330 B1 | 3/2001 | Benderev et al. |
| 6,224,616 B1 | 5/2001 | Kugel |
| 6,273,852 B1 | 8/2001 | Lehe et al. |
| 6,355,053 B1 | 3/2002 | Li |
| 6,406,423 B1 | 6/2002 | Scetbon |
| 6,451,030 B2 | 9/2002 | Li et al. |
| 6,452,450 B1 | 9/2002 | Enriquez |
| 6,464,706 B1 | 10/2002 | Winters |
| 6,478,727 B2 | 11/2002 | Scetbon |
| 6,491,703 B1 | 12/2002 | Ulmsten |
| 6,506,190 B1 | 1/2003 | Walshe |
| 6,575,897 B1 | 6/2003 | Ory et al. |
| 6,582,443 B2 | 6/2003 | Cabak et al. |
| 6,592,515 B2 | 7/2003 | Thierfelder et al. |
| 6,599,323 B2 | 7/2003 | Melican et al. |
| 6,612,977 B2 | 9/2003 | Staskin et al. |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,666,817 B2 | 12/2003 | Li |
| 6,685,629 B2 | 2/2004 | Therin |
| 6,691,711 B2 | 2/2004 | Raz et al. |
| 6,695,855 B1 | 2/2004 | Gaston |
| 6,786,861 B1 | 9/2004 | Pretorius |
| 6,808,486 B1 | 10/2004 | O'Donnell |
| 6,808,487 B2 | 10/2004 | Migliari |
| 6,852,330 B2 | 2/2005 | Bowman et al. |
| 6,884,212 B2 | 4/2005 | Thierfelder et al. |
| 6,884,428 B2 | 4/2005 | Binette et al. |
| 6,911,003 B2 | 6/2005 | Anderson et al. |
| 6,936,052 B2 | 8/2005 | Gellman et al. |
| 6,960,160 B2 | 11/2005 | Browning |
| 6,971,252 B2 | 12/2005 | Therin et al. |
| 7,025,063 B2 | 4/2006 | Snitkin et al. |
| 7,070,556 B2 | 7/2006 | Anderson et al. |
| 7,083,568 B2 | 8/2006 | Neisz et al. |
| 7,121,997 B2 | 10/2006 | Kammerer et al. |
| 7,131,944 B2 | 11/2006 | Jacquetin |
| 7,361,138 B2 | 4/2008 | Wagner et al. |
| 7,878,969 B2 | 2/2011 | Chu et al. |
| 8,043,205 B2 | 10/2011 | MacLean |
| 2002/0078964 A1 | 6/2002 | Kovac et al. |
| 2002/0082619 A1 | 6/2002 | Cabak et al. |
| 2002/0083820 A1 | 7/2002 | Greenhalgh |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0133236 A1 | 9/2002 | Rousseau |
| 2002/0138025 A1 | 9/2002 | Gellman et al. |
| 2002/0147382 A1 | 10/2002 | Neisz et al. |
| 2002/0156476 A1 | 10/2002 | Wilford |
| 2002/0156487 A1 | 10/2002 | Gellman et al. |
| 2002/0161382 A1 | 10/2002 | Neisz et al. |
| 2002/0183762 A1 | 12/2002 | Anderson et al. |
| 2002/0188169 A1 | 12/2002 | Kammerer et al. |
| 2003/0004399 A1 | 1/2003 | Belson |
| 2003/0004580 A1 | 1/2003 | Sump et al. |
| 2003/0004581 A1 | 1/2003 | Rousseau |
| 2003/0065246 A1 | 4/2003 | Inman et al. |
| 2003/0078468 A1 | 4/2003 | Skiba et al. |
| 2003/0078604 A1 | 4/2003 | Walshe |
| 2003/0114865 A1 | 6/2003 | Sater |
| 2003/0114866 A1 | 6/2003 | Ulmsten et al. |
| 2003/0130670 A1 | 7/2003 | Anderson et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0191480 A1 | 10/2003 | Ulmsten et al. |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0004600 A1 | 1/2004 | Yoneno et al. |
| 2004/0005353 A1 | 1/2004 | Lopez-Berestein et al. |
| 2004/0015048 A1 | 1/2004 | Neisz et al. |
| 2004/0015057 A1 | 1/2004 | Rocheleau et al. |
| 2004/0039453 A1 | 2/2004 | Anderson et al. |
| 2004/0039456 A1 | 2/2004 | Davlin et al. |
| 2004/0087970 A1 | 5/2004 | Chu et al. |
| 2004/0097974 A1 | 5/2004 | De Leval |
| 2004/0106847 A1 | 6/2004 | Benderev |
| 2004/0133217 A1 | 7/2004 | Watschke |
| 2004/0144395 A1 | 7/2004 | Evans et al. |
| 2004/0230092 A1 | 11/2004 | Thierfelder et al. |
| 2004/0243166 A1 | 12/2004 | Odermatt et al. |
| 2004/0243178 A1* | 12/2004 | Haut et al. .................. 606/232 |
| 2004/0249240 A1 | 12/2004 | Goldmann et al. |
| 2004/0249397 A1 | 12/2004 | Delorme et al. |
| 2004/0249473 A1 | 12/2004 | Delorme et al. |
| 2004/0267088 A1 | 12/2004 | Kammerer |
| 2005/0004424 A1 | 1/2005 | Raz et al. |
| 2005/0004426 A1 | 1/2005 | Raz et al. |
| 2005/0004427 A1 | 1/2005 | Cervigni |
| 2005/0004576 A1 | 1/2005 | Benderev |
| 2005/0021086 A1 | 1/2005 | De Leval |
| 2005/0043820 A1 | 2/2005 | Browning |
| 2005/0055027 A1 | 3/2005 | Yeung et al. |
| 2005/0065395 A1 | 3/2005 | Mellier |
| 2005/0070829 A1 | 3/2005 | Therin et al. |
| 2005/0080317 A1 | 4/2005 | Merade |
| 2005/0107805 A1 | 5/2005 | Bouffier et al. |
| 2005/0107834 A1 | 5/2005 | Freeman et al. |
| 2005/0234460 A1 | 10/2005 | Miller |
| 2005/0245787 A1 | 11/2005 | Cox et al. |
| 2005/0250977 A1 | 11/2005 | Montpetit et al. |
| 2005/0267325 A1 | 12/2005 | Bouchier et al. |
| 2005/0278037 A1 | 12/2005 | Delorme et al. |
| 2006/0041185 A1 | 2/2006 | Browning |
| 2006/0058578 A1 | 3/2006 | Browning |
| 2006/0089525 A1 | 4/2006 | Mamo et al. |
| 2006/0205995 A1 | 9/2006 | Browning |

(56) References Cited

U.S. PATENT DOCUMENTS

| | | |
|---|---|---|
| 2007/0015953 A1 | 1/2007 | MacLean |
| 2010/0197999 A1 | 8/2010 | Deegan et al. |
| 2010/0198003 A1* | 8/2010 | Morningstar et al. .......... 600/37 |
| 2012/0010462 A1 | 1/2012 | MacLean |

FOREIGN PATENT DOCUMENTS

| | | |
|---|---|---|
| CA | 2427882 A1 | 4/2002 |
| EP | 0632999 A1 | 1/1995 |
| EP | 0643945 A2 | 3/1995 |
| EP | 0677297 B1 | 12/2000 |
| EP | 1191902 A1 | 4/2002 |
| EP | 0774240 B1 | 3/2003 |
| EP | 1342454 A1 | 9/2003 |
| EP | 1345550 A1 | 9/2003 |
| EP | 1333776 B1 | 6/2004 |
| EP | 1324705 B1 | 8/2006 |
| EP | 1079740 B1 | 8/2007 |
| FR | 2811218 A1 | 1/2002 |
| GB | 2382993 A | 6/2003 |
| WO | 95/18571 A1 | 7/1995 |
| WO | 97/13465 A1 | 4/1997 |
| WO | 97/16121 A1 | 5/1997 |
| WO | 98/35632 A1 | 8/1998 |
| WO | 99/59477 A1 | 11/1999 |
| WO | 00/40158 A2 | 7/2000 |
| WO | 00/74594 A1 | 12/2000 |
| WO | 00/74613 A1 | 12/2000 |
| WO | 01/06951 A1 | 2/2001 |
| WO | 01/45588 A2 | 6/2001 |
| WO | 01/78609 A2 | 10/2001 |
| WO | 02/02031 A1 | 1/2002 |
| WO | 02/19945 A2 | 3/2002 |
| WO | 02/26108 A2 | 4/2002 |
| WO | 02/28312 A1 | 4/2002 |
| WO | 02/30293 A1 | 4/2002 |
| WO | 02/39890 A2 | 5/2002 |
| WO | 02/069781 A2 | 9/2002 |
| WO | 02/071953 A2 | 9/2002 |
| WO | 02/078548 A1 | 10/2002 |
| WO | 02/078568 A1 | 10/2002 |
| WO | 03/002027 A1 | 1/2003 |
| WO | 03/002029 A1 | 1/2003 |
| WO | 03/007847 A1 | 1/2003 |
| WO | 03/028584 A2 | 4/2003 |
| WO | 03/032867 A1 | 4/2003 |
| WO | 03/034939 A1 | 5/2003 |
| WO | 03/071962 A2 | 9/2003 |
| WO | 03/073960 A1 | 9/2003 |
| WO | 03/086205 A2 | 10/2003 |
| WO | 03/096929 A1 | 11/2003 |
| WO | 03/096930 A1 | 11/2003 |
| WO | 2004/004600 A1 | 1/2004 |
| WO | 2004/012579 A2 | 2/2004 |
| WO | 2004/012626 A1 | 2/2004 |
| WO | 2004/016196 A2 | 2/2004 |
| WO | 2004/019786 A1 | 3/2004 |
| WO | 2004/045457 A1 | 6/2004 |
| WO | 2005/007079 A2 | 1/2005 |
| WO | 2005/094721 A1 | 10/2005 |
| WO | 2005/112842 A1 | 12/2005 |
| WO | 2005/122721 A2 | 12/2005 |
| WO | 2005/122954 A1 | 12/2005 |
| WO | 2009/102945 A2 | 8/2009 |
| WO | 2012/154742 A1 | 11/2012 |

OTHER PUBLICATIONS

"New Improvements in the Treatment of Female Stress Incontinence", European Association of Urologists, American Medical Systems, Mar. 2003, 34 pages.

"The Confident approach to curing incontinence", Monarch Subfascial hammock, American Medical Systems, 5 pages.

Kovac, et al., "Pubic Bone Suburethral Stabilization Sling for Recurrent Urinary Incontinence", Obstetrics & Gynecology, vol. 89, No. 4, Apr. 1997, pp. 493-642. Retrieved from: http://journals.lww.com/greenjournal/Abstract/1997/04000/Pubic_Bone.

Palma et al., "Safyre: A Readjustable Minimally Invasive Sling for Female Urinary Stress Incontinence", SafyrenTM, International Journal of the Brazilian Society of Urology, vol. 29 No. 4, 2003, pp. 353-359.

Siegel, A. L., "Vaginal Mesh Extrusion Associated with use of Mentor Transobturator Sling", Elsevier, Inc., Adult Urology, 2005, pp. 995-999.

Dargent et al., "Insertion of a sub urethral sling through the obturating membrane in the treatment of female urinary incontinence", Gynécol Obstét Fertil, vol. 30, 2002, pp. 576-582.

Dargent et al., "Pose d'un ruban sous uretral oblique par voie obturatrice dans le traitement de l'incontinence urinaire feminine", Gynécol Obstét Fertil, vol. 30, 2002, 1 page.

De Leval, J., "Novel Surgical Technique for the Treatment of Female Stress Urinary Incontinence: Transobturator Vaginal Tape Inside-Out", European Urology vol. 44, 2003, pp. 724-730.

Delorme et al., "Transobturator Tape (Uratape®): A New Minimally-Invasive Procedure to Treat Female Urinary Incontinence", European Urology 45, 2004, pp. 203-207.

Delorme, E., "The transobdurator band: a minimmaly invasive procedure for treatment of urinary stress incontinence in women", Progress in Urology, vol. 11, 2001, pp. 1306-1313.

Hermieu et al., "Les bandelettes sous-urétrales synthétiques dans le traitement de l'incontinence urinaire d'effort féminine", Progrés en Urologie, vol. 13, 2003, pp. 636-647.

Ingelman-Sundberg et al., "Surgical Treatment of Female Urinary Stress Incontinence", Contr. Gynec Obstet, vol. 10, 1983, pp. 51-69.

Nickel, R. F., "Transpelvic Sling Urethroplasty with and without Colpususpension for the Treatment of Complicated Urinary Incontinence in Bitches", Third Annual Scientific meeting (ECVS), Riccione, Jun. 23-26, 1994.

Final Office Action for U.S. Appl. No. 13/242,821, mailed Nov. 20, 2013, 12 pages.

RCE and Office Action Response for U.S. Appl. No. 13/242,821, filed Feb. 19, 2014, 11 pages.

Non-Final Office Action for U.S. Appl. No. 13/242,821, mailed Mar. 7, 2014, 11 pages.

Final Office Action for U.S. Appl. No. 131242,821, mailed on Feb. 9, 2015, 6 pages.

* cited by examiner

ANCHORS FOR BODILY IMPLANTS AND METHODS FOR ANCHORING BODILY IMPLANTS INTO A PATIENT'S BODY

CROSS-REFERENCE TO RELATED APPLICATION

This application is a Nonprovisional of, and claims priority to, U.S. patent application Ser. No. 61/485,388, filed May 12, 2011, entitled "ANCHORS FOR BODILY IMPLANTS AND METHODS FOR ANCHORING BODILY IMPLANTS INTO A PATIENT'S BODY", which is incorporated by reference herein in its entirety.

BACKGROUND

1. Field

The invention generally relates to medical devices and procedures, and more particularly to anchors for bodily implants and methods for anchoring the bodily implants into a patient's body.

2. Description of the Related Art

A common practice while inserting bodily implants, such as slings used in the treatment of urinary incontinence or fecal incontinence, is to use anchors. An anchor assists in holding a bodily implant and prevents it from being dislodged from its intended location with respect to an anatomy of a patient's body. The anchor works by engaging with surrounding anatomy and creating sufficient force to hold the bodily implant in its intended position.

Existing anchors are designed with anchoring protrusions. These protrusions vary in size based on the holding force required to anchor the bodily implants. In some existing anchors, the greater the holding force required, the longer the protrusions are. In some existing anchors, the protrusions are sharpened at their distal ends to ensure engagement of the anchors with surrounding tissues within the patient's body. However, it may be undesirable to leave the bodily implants, which have sharp edges protruding outwards, within the patient's body as the sharp edges may damage the surrounding tissues causing pain and discomfort. Further, such anchors may also cause damage to internal tissues of the patient's body during insertion and removal of anchors.

Thus, there is a need for an anchor that precludes the need for protrusions with sharp edges. Further, there is a need for an anchor that can exert a holding force on a bodily implant to anchor it at a suitable location in the patient's body.

SUMMARY

An anchor is provided for anchoring a bodily implant within a body of a patient. The anchor includes an implant engaging portion for engaging the bodily implant, wherein the implant engaging portion is disposed on a lateral portion of the anchor. The anchor further includes a distal end portion configured to pass through a passageway in the patient's body, the passageway defining a first axis and a proximal end portion disposed longitudinally opposite to the distal end portion on the anchor. The anchor defines a second axis extending from the distal end portion to the proximal end portion. The anchor is configured to rotate when a force is applied to the bodily implant such that the second axis defined by the anchor forms an angle with the first axis defined by the passageway.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating urinary incontinence. As described below in various illustrative embodiments, the invention provides systems, methods, and devices employing an improved soft tissue anchor termed as anchor for anchoring an end of a bodily implant in place, at least temporarily within a body of a patient. In accordance with several other embodiments, the invention may be used for the treatment of fecal incontinence as well.

The term patient may be used for a person who benefits from the anchors disclosed in the present invention. For example, the patient can be a person whose body receives the bodily implant with the disclosed anchor at its end in a surgical treatment. For example, in some embodiments, the patient may be a human female, a human male, or any other mammal.

The terms proximal and distal described in relation to various devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like who may perform the procedure of delivery and placement of the bodily implants into the patient's body as described in the present invention. The term proximal refers to an area or portion that is closer or closest to the operator during a placement procedure. The term distal refers to an area or portion that is further or farthest from the operator.

Figure 1:
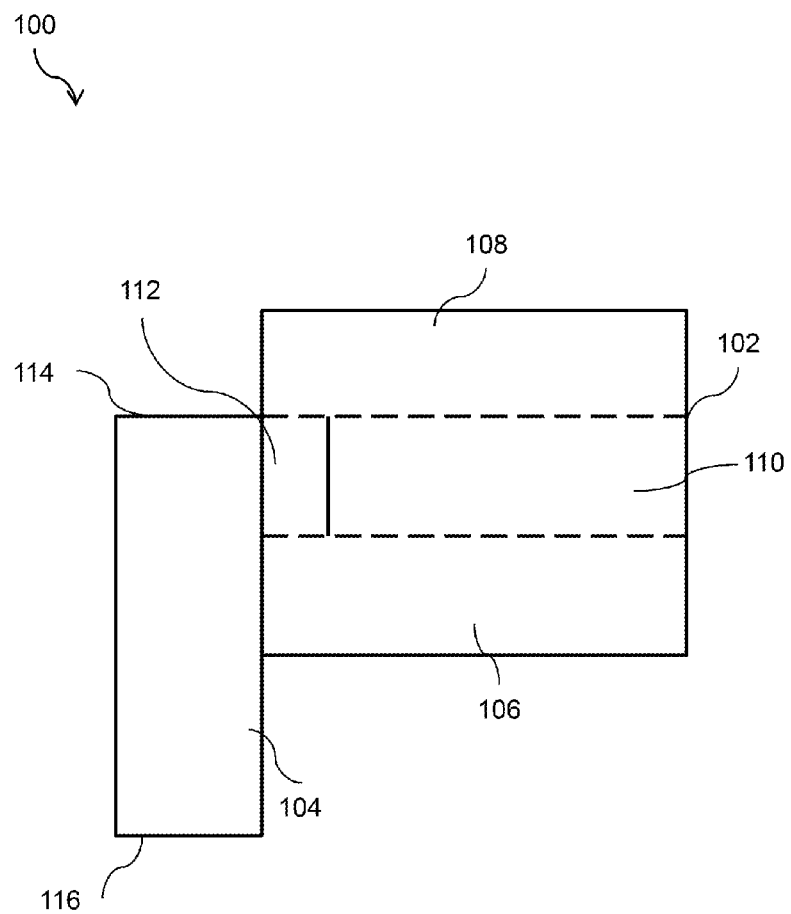
FIG. 1 is a schematic diagram of an anchor affixed to an end portion of a bodily implant, in accordance with an embodiment of the present invention.

FIG. 1 is a schematic diagram of an anchor 102 affixed to an end portion of a bodily implant 104, in accordance with an embodiment of the present invention. The anchor 102 and the bodily implant 104 that are configured to be placed inside a patient's body can together be hereafter referred to as a medical device 100 for the simplicity of the description.

The anchor 102 includes a proximal end portion 106, a distal end portion 108, and a medial portion 110. The distal end portion 108 is configured to pass through a passageway in the patient's body. For example, in some embodiments, the distal end portion 108 is configured to pass through a passageway that is formed during insertion of the anchor 102. In some embodiments, the passageway defines a first axis A. The proximal end portion 106 is disposed longitudinally opposite to the distal end portion 108 on the anchor 102 such that the proximal end portion 106 and the distal end portion 108 lie at two ends of the anchor 102. The medial portion 110 (that, in some embodiments, integrally forms a middle part of the anchor 102 between the proximal end portion 106 and the distal end portion 108) further includes an implant engaging portion 112 for engaging the bodily implant 104. The implant engaging portion 112 is disposed on a lateral or side portion of the anchor 102 such that the bodily implant 104 is asymmetrically attached to the anchor 102. Further, the implant engaging portion 112 extends from the proximal end portion 106 toward the distal end portion 108 such that the longitudinal axis of the implant engaging portion 112 is parallel to the longitudinal axis of the anchor 102.

The bodily implant 104 can be coupled to the implant engaging portion 112 in various ways. There can be different types of mechanisms to couple the bodily implant, in accordance with various embodiments. For example, the bodily implant 104 can be pierced within the implant engaging portion 112 and subsequently glued, stapled, or tied to the implant engaging portion 112. Numerous types of designs of the implant engaging portion 112 are possible depending on the nature of mechanism of engaging the bodily implant 104.

In accordance with some embodiments, the implant engaging portion 112 includes at least one protuberance for engaging the bodily implant 104 therewith. The at least one protuberance is designed to extend longitudinally from a lower portion of the implant engaging portion 112 and configured to hold the bodily implant 104 at place. The at least one protuberance may be a small extension or projection extending from the lateral or side portion of the anchor 102.

In some embodiments, there can be only one protuberance. In some other embodiments, there can be two protuberances, a first protuberance and a second protuberance. The first and the second protuberances are configured so that the bodily implant 104 can be pierced through them and fixed therein. In some embodiments, the first protuberance and the second protuberance are configured to interlock with each other and engage the bodily implant 104 therein. In accordance with these embodiments, the first protuberance may include a male coupling member and the second protuberance may include a female coupling member such that the coupling members may fit in an interlocked manner.

In some embodiments, the at least one protuberance may include a movable locking mechanism for engaging the bodily implant 104. The movable locking mechanism may be configured to latch or lock the bodily implant 104 to fixedly couple the implant 104 to the engaging portion 112. In some embodiments, the movable locking mechanism may be operated through a sliding mechanism such that the bodily implant 104 is latched or coupled to the implant engaging portion 112 by slidably moving the at least one protuberance relative to the anchor 102. At least one opening may be provided on the implant engaging portion 112 such that the at least one protuberance may slidably fit into the at least one opening.

In still various other embodiments, several types of locking, latching, and engaging mechanisms may be provided on the implant engaging portion 112 that are capable of holding and engaging the bodily implant 104.

In embodiments, the anchor 102 is elongated in nature such that a length of the anchor 102 which extends longitudinally is substantially more than a width of the anchor 102 which extends transversely. The anchor 102 defines an axis (second axis B) extending from the distal end portion 108 toward the proximal end portion 106.

The proximal end portion 106 and the distal end portion 108 may have any suitable size and shape. In some embodiments, the distal end portion 108 is substantially conical. In other embodiments, the distal end portion 108 may be substantially rectangular, circular, and the like. In some embodiments, the proximal end portion 106 is substantially cylindrical. In other embodiments, the proximal end portion 106 is substantially rectangular, circular, and the like. A tip portion of the distal end portion 108 that is configured to pass through the passageway in the patient's body may be shaped conically and sharp in nature. In general, the anchor 102 may have any shape and size that is suitable for affixing the anchor 102 within an anatomical membrane, muscle, ligament, soft tissue, bone or any other anatomical site.

In some embodiments, the anchor 102 may be made of any suitable biocompatible material. In other embodiments, the anchor 102 may be made, for example, of a synthetic material such as nylon, polyethylene, polyester, polypropylene, fluoropolymers or a co-polymer thereof. In some other embodiments, they may be formed, at least in part, from a mammalian tissue material such as bovine, porcine, equine, human cadaveric or engineered tissue. In still other embodiments, the material of the anchor 102 may include a combination of synthetic and mammalian tissue/biocompatible materials. In some embodiments, the anchor 102 is made of a metal, ceramic, polymer, magnet, or an alloy.

According to some embodiments, at least a portion of the anchor 102 is biodegradable and may also dissolve and/or be absorbed by the patient's tissues. Exemplary biodegradable materials that may be employed for at least a portion of the anchor 102 include, but are not limited to, polylactic acid, polyglycolic acid, and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly (glycolide-co-trimethylene carbonate) (PGA/PTMC), poly (D,L-lactide-co-caprolactone) (PLA/PCL), and poly (glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, polyphosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof.

In some embodiments, the anchor 102 may be configured to be dissolved within a particular time range. The anchor 102 may be configured, for example, to substantially absorb (or have a portion that substantially absorbs) into the patient's tissues within about 2, 4, 6 or 8 or more weeks from the time the bodily implant 104 is implanted. Preferably, the anchor 102 remain structurally intact long enough for scar tissue and/or other neighboring cells or tissues to grow into the bodily implant 104 to effectively anchor it in place.

The bodily implant 104 that is affixed with the use of the anchor 102 is configured to be placed within the patient's body and support a portion of the body. For example, the bodily implant 104 can be shaped and sized to support a portion of the body around a bladder, urethra, anal canal, rectum, and anus of the patient. The bodily implant 104 has a first end portion 114 and a second end portion 116 such that the bodily implant 104 extends along a length between the first end portion 114 and the second end portion 116. The length and width of the bodily implant 104 may vary based on its intended use. The bodily implant 104 can be of a variety of sizes, shapes, and configurations depending on the intended use and locations of placement of the bodily implant 104.

In some embodiments, the bodily implant 104 is formed of a material that allows tissue in-growth after implantation. Various types of woven tapes, fabrics, or meshes may be utilized in the fabrication and manufacturing of the bodily implant 104, in accordance with various embodiments of the present invention. The bodily implant 104 may utilize a variety of mesh materials and may be designed in a variety of forms. An example of a mesh utilized in the bodily implant 104 is Polyform® Synthetic Mesh developed by the Boston Scientific Corporation. The Polyform® Synthetic Mesh is made from uncoated monofilament macro-porous polypropylene. The bodily implant 104 may also be made from a biological material or a cadaveric tissue. In some embodiments, the bodily implant 104 has a smooth surface. In such embodiments, the smooth surface may avoid or reduce irritation on adjacent body tissues during mesh-tissue interactions. Additionally, the bodily implant 104 may be stretchable and flexible to adapt movements in accordance with the anatomy of the human body and reduce suture or anchor pullout. Furthermore, softness, lightness, conformity, and strength are certain other attributes required in the bodily implant 104 for efficient tissue repair and implantation. In an embodiment, the bodily implant 104 can have a coating. For example, the bodily implant 104 can be coated with an antimicrobial agent and/or an antifungal agent.

FIG. 2A-2D illustrate perspective views of an anchor 202 for affixing an end portion of a bodily implant such as the bodily implant 104 as illustrated in FIG. 1, in accordance with an embodiment of the present invention. As depicted, the anchor 202 includes a proximal end portion 204, a distal end portion 206 and a medial portion 208.

The distal end portion 206 is configured to pass through a passageway in the patient's body such that the passageway defines a first axis A. In some embodiments, the distal end portion 206 is configured to create the passageway as it is inserted into the body of the patient. The proximal end portion 204 is disposed longitudinally opposite to the distal end portion 206 on the anchor 202. The medial portion 208 further includes an implant engaging portion 210 for engaging the bodily implant. The implant engaging portion 210 is disposed on a lateral or side portion of the anchor 202 such that the bodily implant is asymmetrically attached to the anchor 202. The implant engaging portion 210 extends axially from the proximal end portion 204 toward the distal end portion 206 and positioned asymmetrically at a lateral part of the medial portion 208. The term asymmetric attachment means that the bodily implant is coupled at only one side of the longitudinal axis of the anchor 202 and not on both sides. The effect of asymmetric attachment is available along only one lateral side rather than on the longitudinal axis at the center of the anchor 202.

According to some embodiments, the implant engaging portion 210 is formed integrally with the medial portion of the anchor 208. In other embodiments, the implant engaging portion 210 is separable from the medial portion 208 such that it is configured to removably fit into the medial portion 208. The anchor 202 defines a second axis B extending from the distal end portion 206 toward the proximal end portion 204. The second axis B coincides with the longitudinal axis along the length of the anchor 202.

As illustrated in FIGS. 2A-2D, the implant engaging portion 210 further includes two protuberances, a first protuberance 212a and a second protuberance 212b. There can be different types of mechanisms to couple the bodily implant through the first protuberance 212a and the second protuberance 212b, in accordance with various embodiments. For example, the bodily implant can be pierced through the protuberances 212a and 212b, and subsequently glued, stapled, or tied. Numerous types of designs of the protuberances 212a and 212b are possible depending on the nature of mechanism for engaging the bodily implant.

Figure 2A:
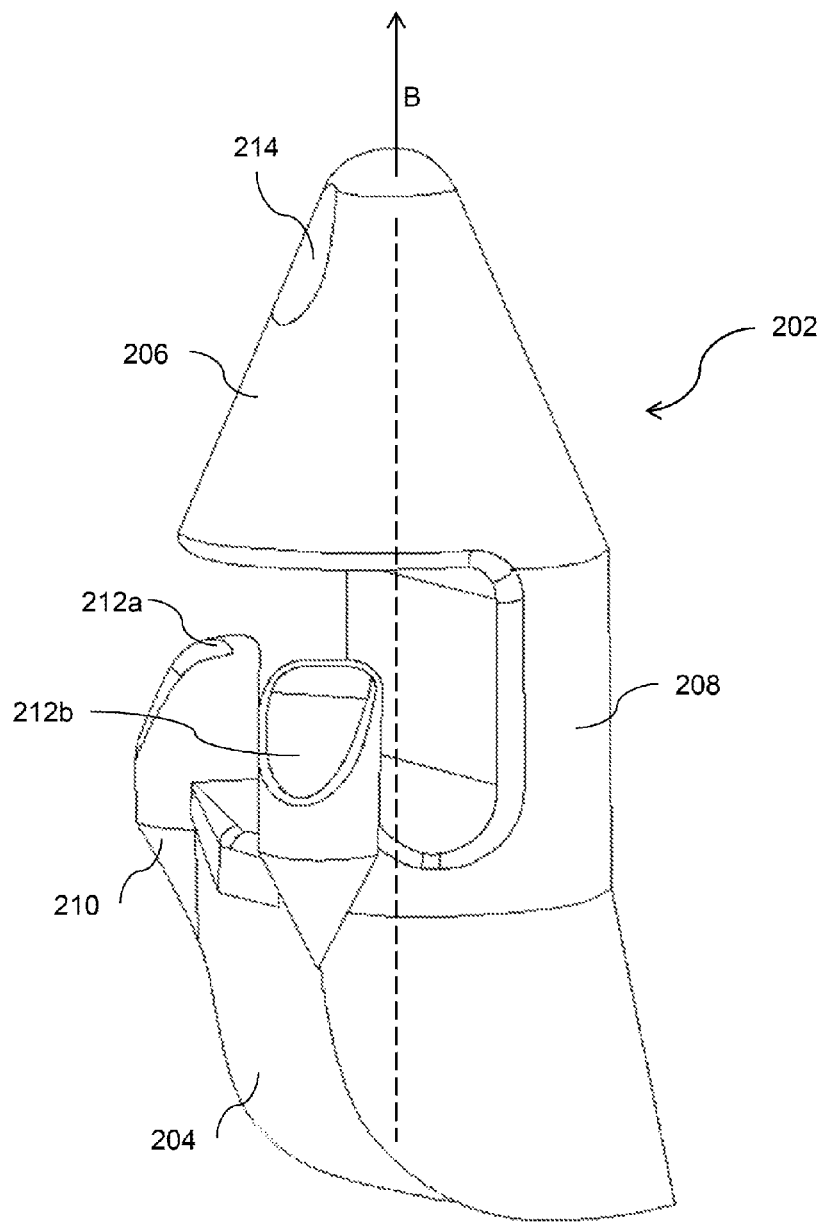
FIGS. 2A-2D illustrate perspective views of an anchor for affixing an end portion of a bodily implant, in accordance with various embodiments of the present invention.

In some embodiments, the first protuberance 212a and the second protuberance 212b are designed to extend longitudinally from a lower portion of the implant engaging portion 210 and configured to hold the bodily implant at place. The protuberances 212a and 212b may be designed in the form of small extensions or projections extending from the lateral or side portion of the anchor 202, as illustrated in FIG. 2A.

Figure 2B:
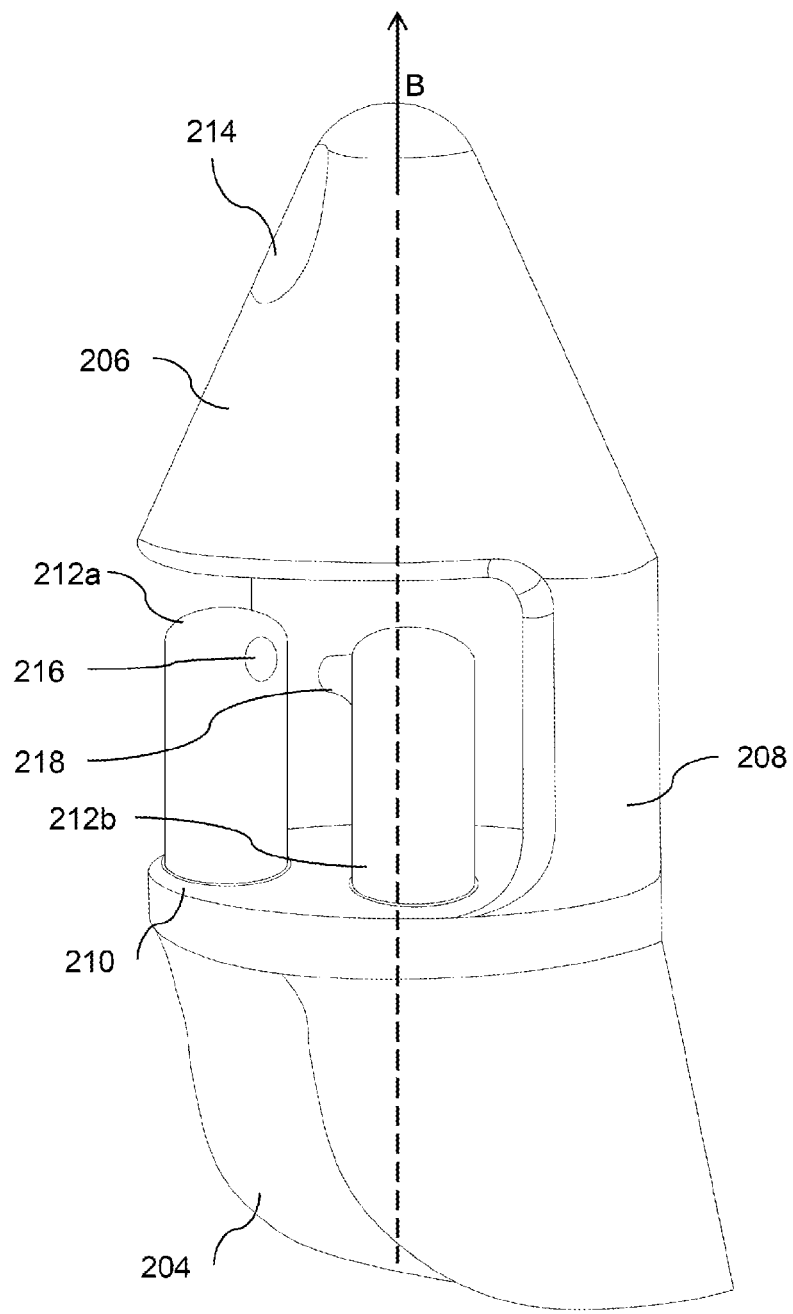

In some embodiments, the first protuberance 212a and the second protuberance 212b are configured to interlock with each other and engage the bodily implant therein. In accordance with these embodiments, the first protuberance 212a may include a female coupling member 216 and the second protuberance 212b may include a male coupling member 218, as shown in FIG. 2B. The coupling members 216 and 218 can fit into one another for interlocking.

Figure 2C:
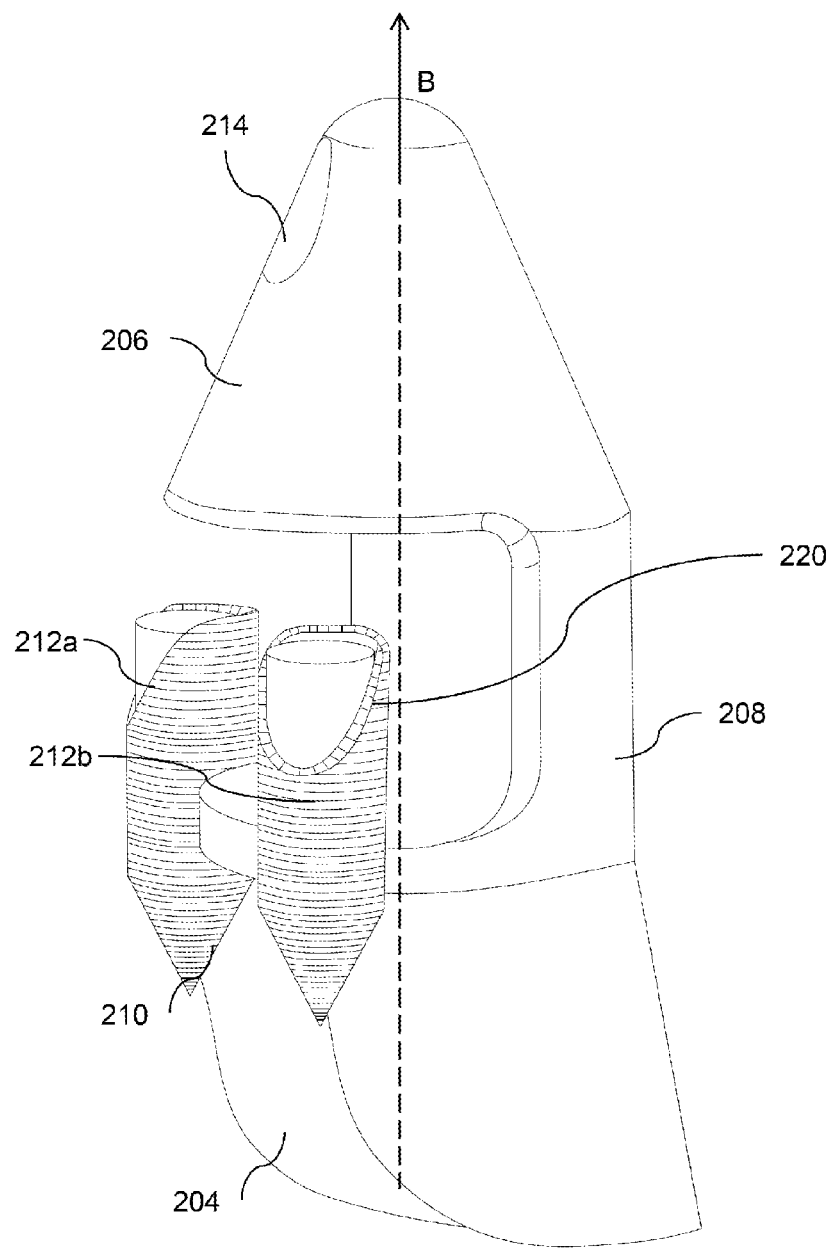
Figure 2D:
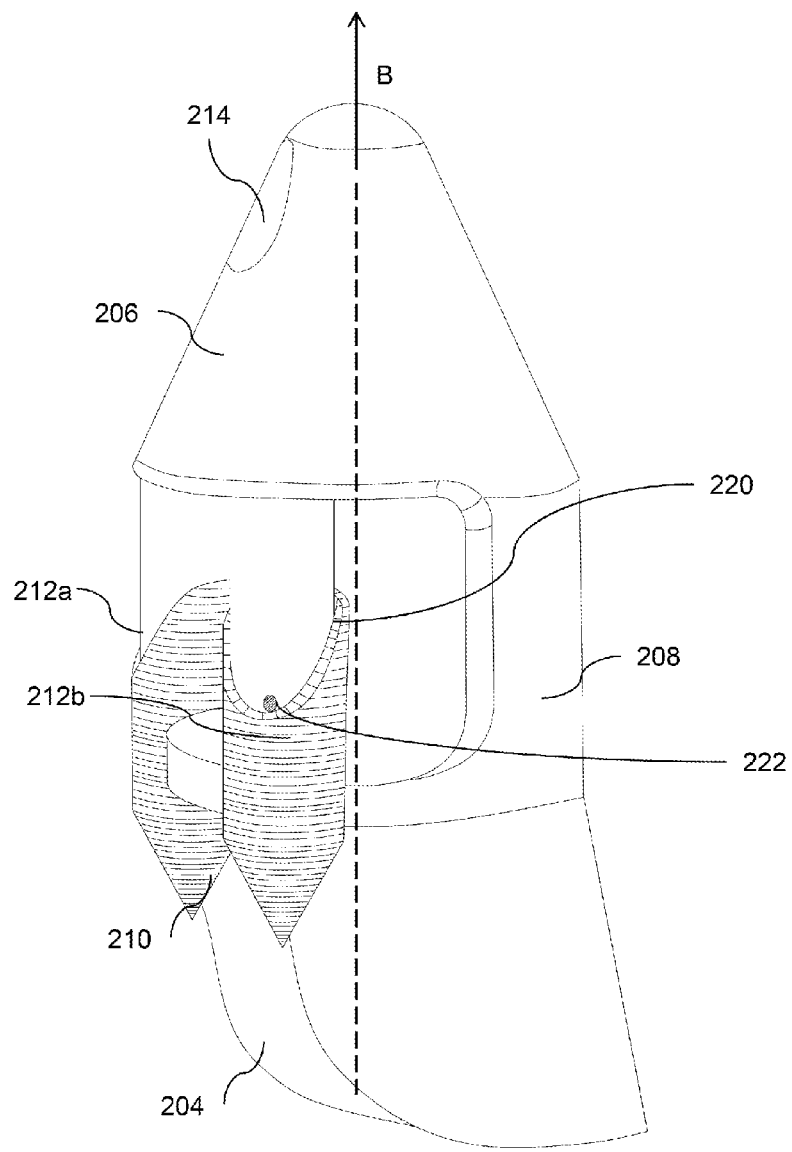

In some embodiments, the first protuberance 212a and the second protuberance 212b may include a movable locking mechanism 220 for engaging the bodily implant, as shown in FIGS. 2C and 2D. The movable locking mechanism 220 may be configured to latch or lock the bodily implant to fixedly couple the implant to the engaging portion 210. In some embodiments, the movable locking mechanism 220 may be operated through a sliding mechanism such that the bodily implant is latched or coupled to the implant engaging portion by slidably moving the protuberances 212a and 212b relative to the anchor 102. FIG. 2D shows a latched configuration achieved after sliding. A latch 220 may be provided with the sliding mechanism 220 to retain the protuberances 212a and 212b in the latched configuration. Two openings (not shown) may be provided on the implant engaging portion 210 such that the protuberances 212a and 212b may slidably fit into the openings.

In still various other embodiments, several types of locking, latching, and engaging mechanisms may be provided that are capable of locking and latching the body implant with the protuberances 212a and 212b. In accordance with various embodiments, the first protuberance 212a and the second protuberance 212b are designed to be projectionless and barbless such that these protuberances, specifically their tip portions do not harm and irritate the body tissues.

The anchor 202 can have a variety of shapes and sizes similar to the anchor 102 as described in conjunction with FIG. 1. Similarly, the material and composition of the anchor 202 can vary as described in conjunction with FIG. 1.

As illustrated in FIGS. 2A-2D, the anchor 202 includes or defines a first opening or lumen 214 defined on the distal end portion 206 of the anchor 202. The first opening 214 is disposed on the distal end portion 206 such that the lateral ends of the first opening 214 passes through two conical edges of the distal end portion 206. A second opening or lumen (not shown) is provided on the proximal end portion 204. The second opening can be provided at a lateral surface of the proximal end portion 204 or at a bottom surface of the anchor 202. In some embodiments, the second opening is asymmetrically disposed on the anchor 202 such that a distance of the second opening from a first lateral edge of the anchor 202 is more than a distance of the second opening from a second lateral edge of the anchor 202. In some embodiments, the second opening may extend from a lateral edge of the anchor 202 to a bottom portion of the anchor 202. In accordance with various embodiments, the shape and size of the first and the second openings (hereafter referred to as openings together) may vary based on the intended use and the requirements.

Figure 3:
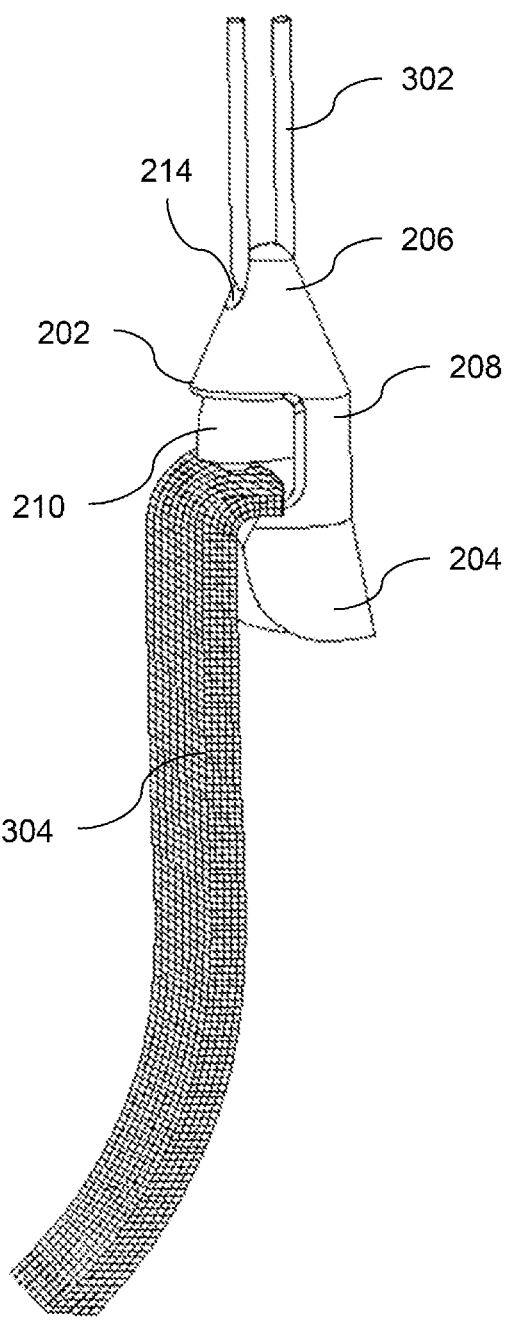
FIG. 3 is a perspective view of an anchor with a delivery lead coupled to a distal end portion of the anchor, in accordance with an embodiment of the present invention.
Figure 4:
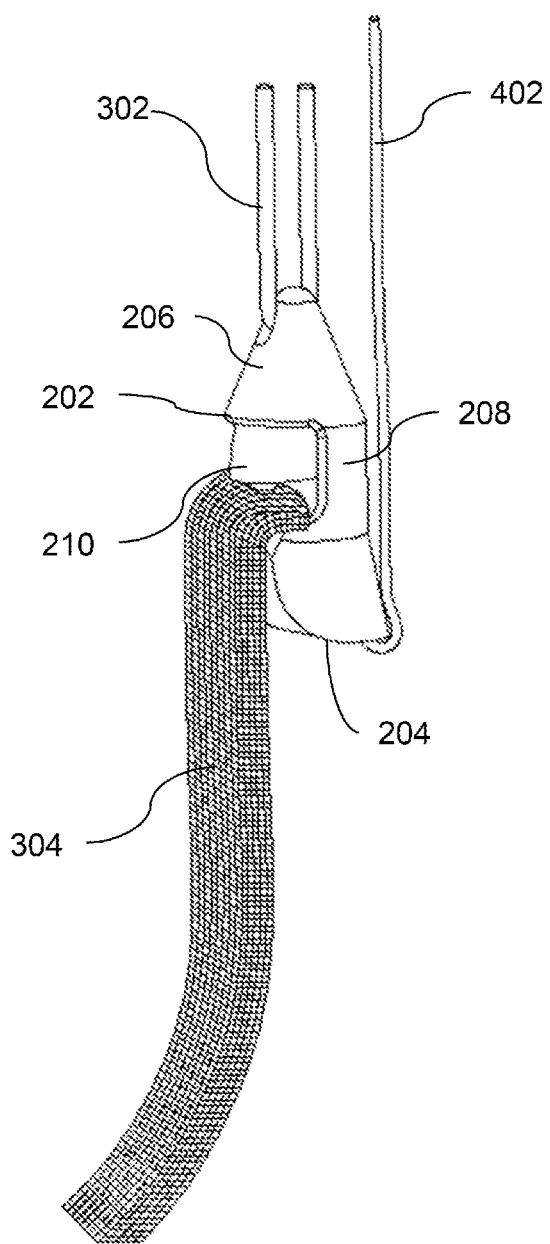
FIG. 4 is a perspective view of an anchor with a tilt control lead coupled to a proximal end portion of an anchor, in accordance with an embodiment of the present invention.
Figure 5:
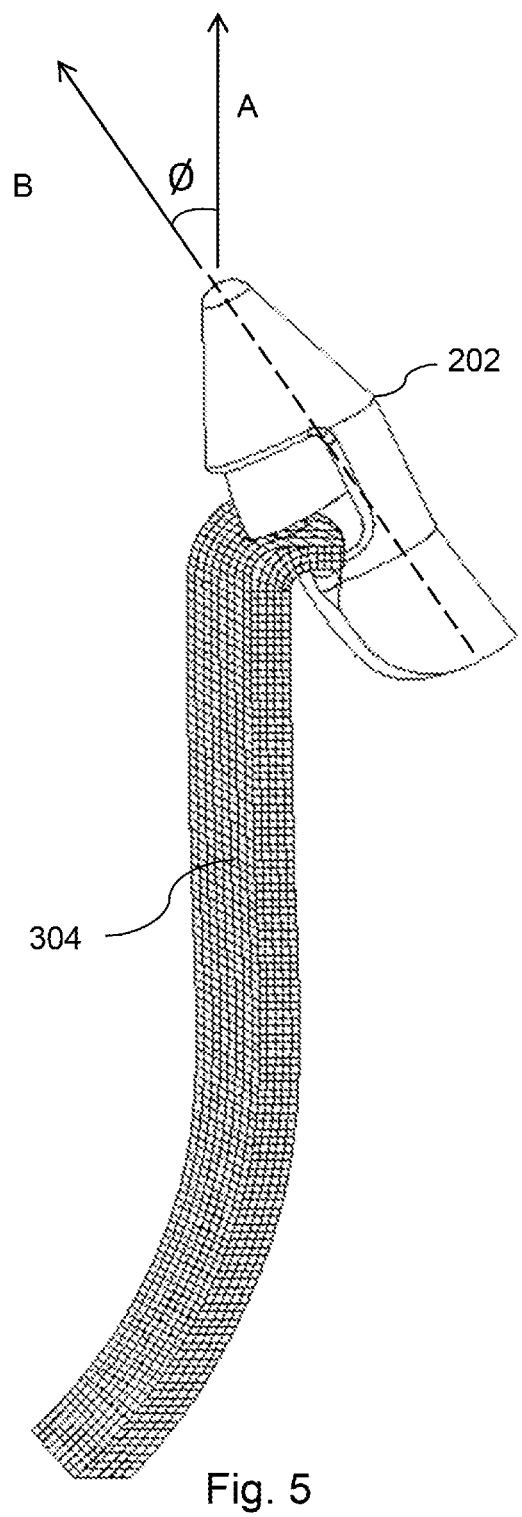
FIG. 5 is a perspective view of an anchor in a rotated configuration depicting an angle formed between a first axis and a second axis.
Figure 6:
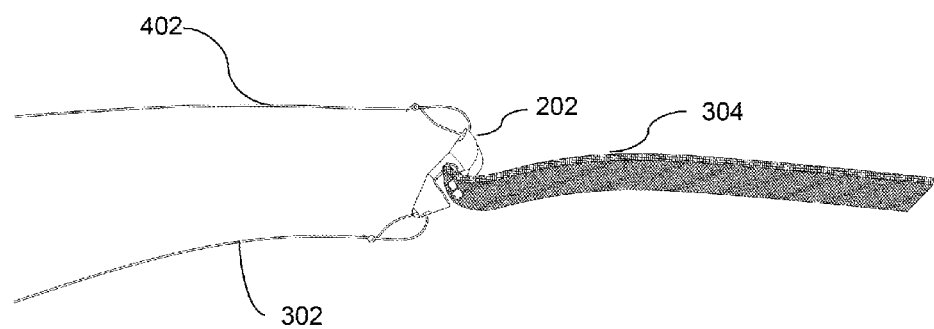
FIG. 6 is a perspective view of an anchor coupled to a delivery lead and a tilt control lead, in accordance with another embodiment of the present invention.

The first opening 214 is defined to receive and engage a first lead termed as a delivery lead 302 with the anchor 202, as illustrated in FIG. 3. In some embodiments, the delivery lead can include a loop at one of its end portions configured to be coupled to a delivery tool such as a surgical needle. In some embodiments, the loop may be some kind of a suture loop. The delivery lead 302 can be brought though body tissues to assist in the delivery of a bodily implant such as the bodily implant 304. The anchor 202 can be forced into the passageway within the body tissues by applying forces on the delivery lead 302. As illustrated in FIG. 4, the second opening is defined to receive and engage a second lead termed as a tilt control lead 402. The tilt control lead 402 can be brought through the body tissues along with the delivery lead 302. The tilt control lead 402 is used to rotate the anchor 202 such that an angle Ø is formed between the first axis A (defined by the passageway) and the second axis B (defined by the anchor) in FIG. 5. The angle Ø thus formed assists in anchoring the bodily implant such as the bodily implant 304 with the body tissues. FIG. 6 illustrates a perspective view of the delivery lead 302 and the tilt control lead 402 coupled to the anchor 202. As shown, the leads 302 and 402 can form a loop at the coupling end such that the leads 302 and 402 can be removed easily after placement of the anchor 202 by cutting the loops.

Figure 7A:
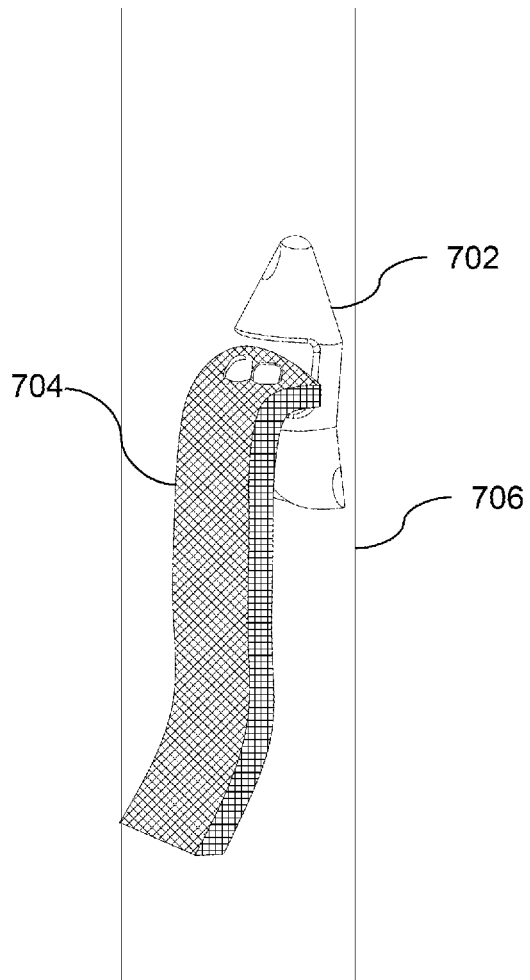
FIG. 7A illustrates an exploded perspective view of an anchor within a bodily passageway during delivery.
Figure 7B:
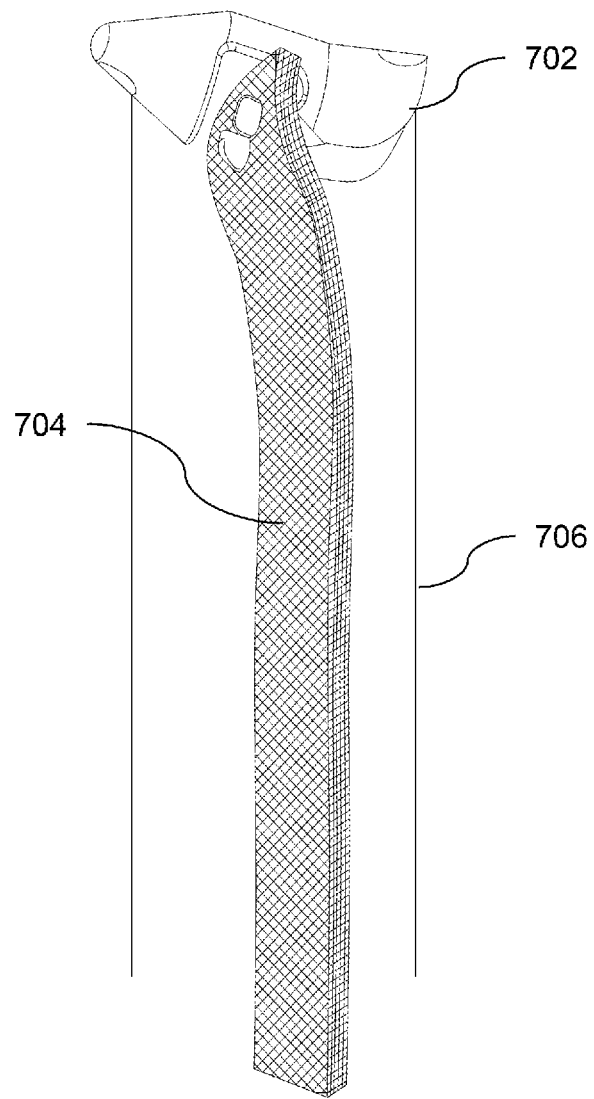
FIG. 7B illustrates an exploded perspective view of an anchor within a bodily passageway after being rotated by an angle.

FIG. 7A illustrates an exploded perspective view of an anchor 702 within a bodily passageway 706 during delivery. The anchor 702 is coupled to a bodily implant 704. The longitudinal axis of the anchor 702 is substantially parallel to the direction of the bodily passageway 706 during delivery. FIG. 7B illustrates an exploded view of the anchor 702 after being rotated by an angle upon placement. In this configuration, the anchor 702 engages with the bodily tissues since the length of the anchor 702 (along its longitudinal axis) is more than its width. The measure of the angle by which the anchor 702 is rotated can vary depending on the amount of rotational torque or turning momentum generated to cause the rotation of the anchor 702.

Figure 8A:
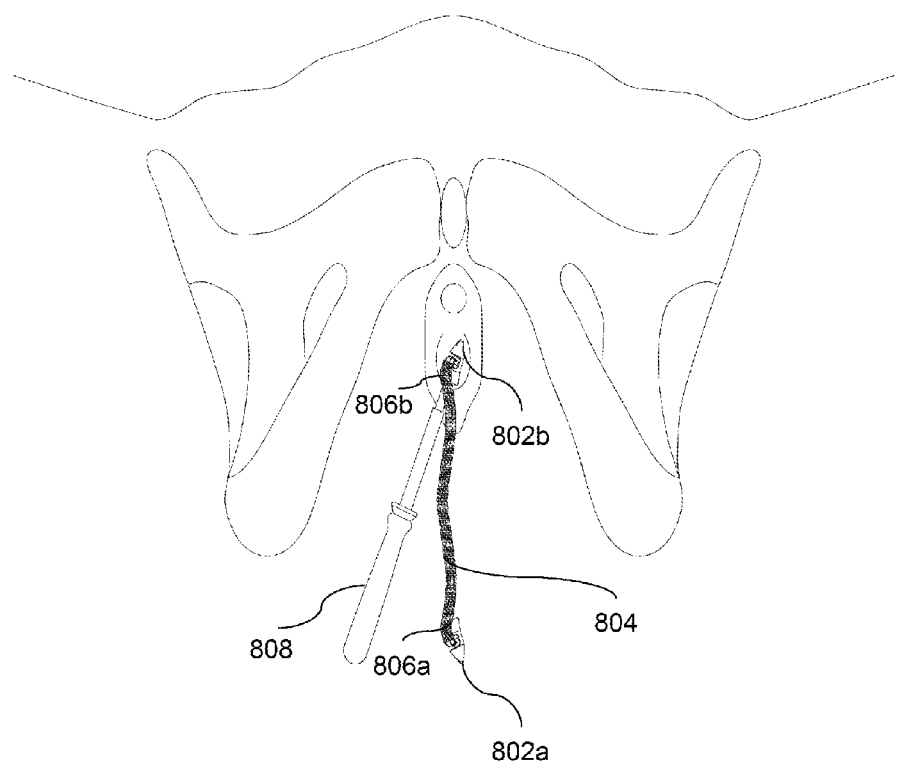
FIGS. 8A and 8B depict an illustrative method of implanting a bodily implant in a periurethral tissue of a patient, in accordance with an embodiment of the present invention.
Figure 8B:
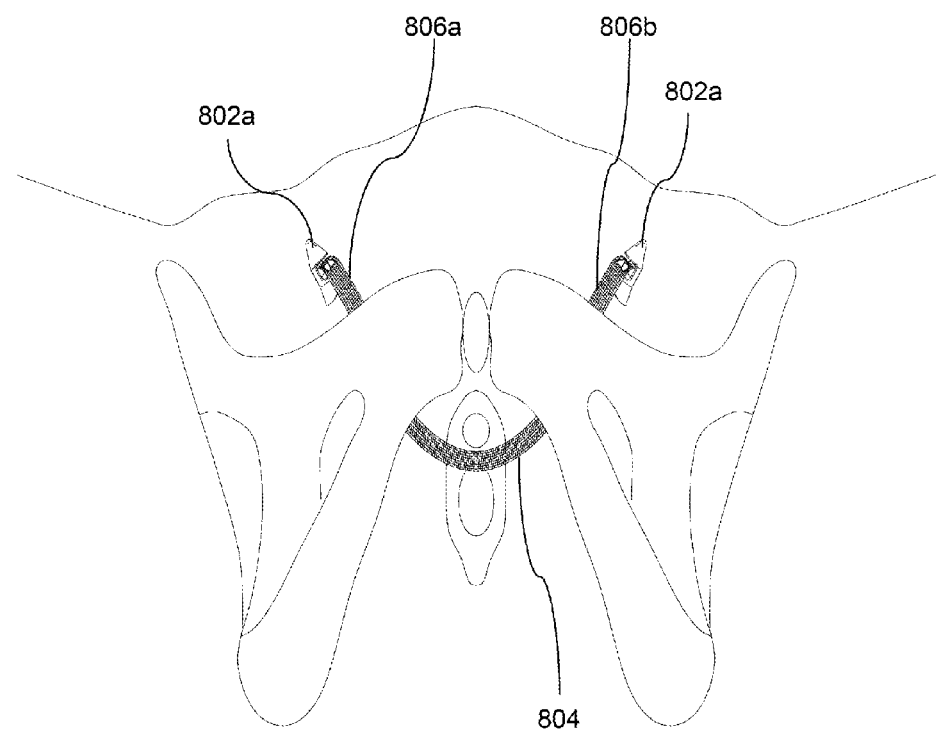

FIGS. 8A and 8B depict an illustrative method of implanting a bodily implant such as the bodily implant 804 in a periurethral tissue of a patient to form a platform under a urethra of the patient. As illustrated in FIG. 8A, a first anchor 802a is fitted on a first end portion 806a of the bodily implant 804 and a second anchor 802b is fitted on a second end portion 806b of the bodily implant 804. The two anchors 802a and 802b are configured to anchor and hold the bodily implant 804 at two end portions 806a and 806b such that the bodily implant 804 is fixedly supported inside the body tissues in an appropriate tension. In some embodiments, at least one of the anchors 806a and 806b are similar to the anchor 102 illustrated in conjunction with FIG. 1. In other embodiments, at least one of the anchors 806a and 806b are similar to the anchor 202 illustrated in conjunction with FIG. 2.

Figure 9:
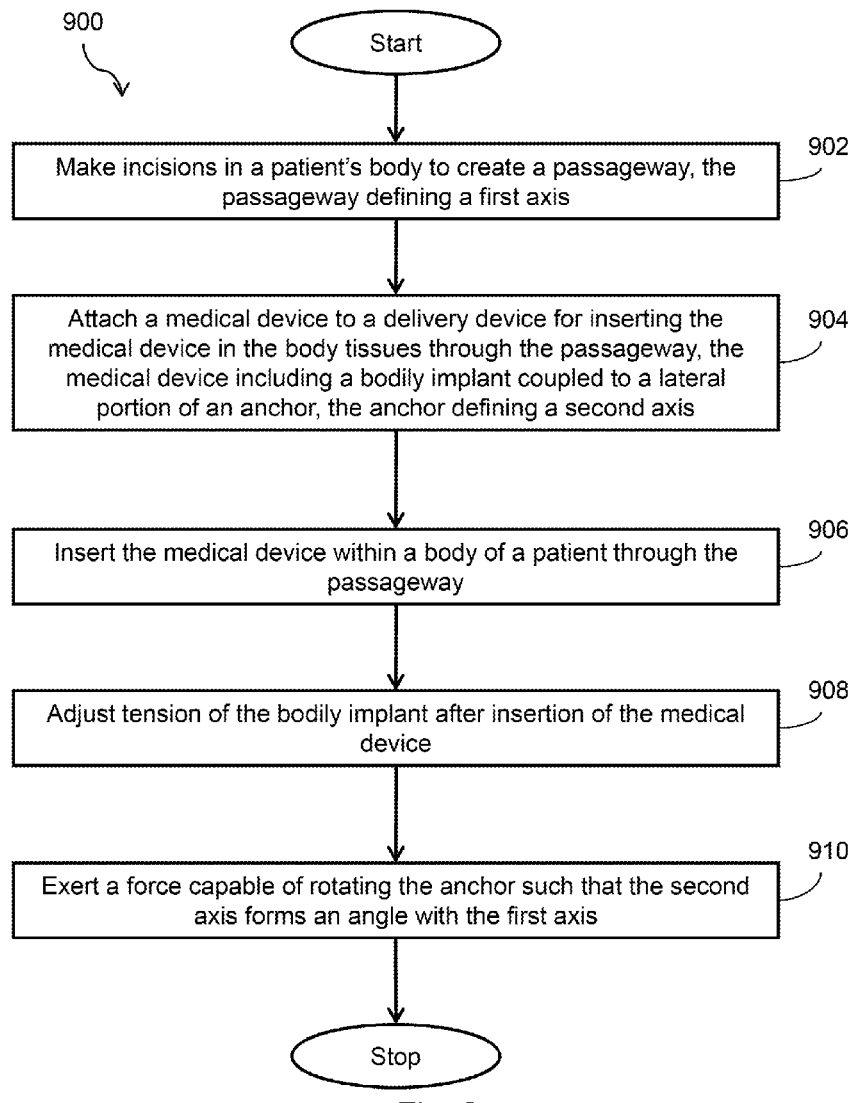
FIG. 9 is a flowchart illustrating a method of implanting a bodily implant in a body of a patient, in accordance with an embodiment of the present invention.

FIG. 9 is a flowchart illustrating a method 900 for anchoring a bodily implant such as the bodily implant 804 within a body of a patient. In accordance with various embodiments, an anchor such as the anchor 802a can be used to fix the bodily implant 804 in place. The anchor 802a has a length that is substantially more than its width. During delivery, the anchor 802a is inserted along a longitudinal direction, which is parallel to axis of the bodily passageway. After insertion, the anchor 802a is rotated by an angle with respect to the bodily passageway. In this configuration, the longitudinal direction of the anchor 802a is substantially perpendicular to the passageway. Since the length of the anchor 802a is more than the width of the bodily passageway, the anchor 802a gets engaged within the bodily tissues. Similarly, the anchor 802b can also be used to fix the other end of the bodily implant 804. The configuration of the anchor (during delivery and after rotation) is illustrated in FIGS. 7A and 7B, respectively.

Referring now to FIGS. 8A, 8B, and 9 together, a specific method for implanting and anchoring a bodily implant such as the bodily implant 804 is described in accordance with an embodiment of the present invention. At step 902, an incision is made in an anterior vaginal wall and dissected bilaterally to the interior portion of an inferior pubic ramus of the patient. The vaginal incision creates a passageway from the vaginal opening to urethral sphincter that is responsible for controlling the flow of urine. The vaginal incision allows the bodily implant 804 to be placed correctly under the urethra, without passing a delivery tool 808 through the retropubic space and abdominal wall unknowingly causing damage. The direction of the passageway defines a first axis. The first axis is along the direction of insertion through the body tissues. In some embodiments, an operator further makes second and third incisions in groin areas—one on a left groin area and the other on a right groin area on either side of the pubis. In other embodiments, the second and the third incisions can be made in the obturator membrane or in the abdomen.

At step 904, the operator attaches/couples a medical device to the delivery tool 808. The medical device includes the bodily implant 804 coupled to lateral portions of the anchors 802a and 802b at its two end portions 806a and 806b as illustrated in FIGS. 8A and 8B. For example, a first anchor 802a is coupled to a first end portion 806a of the bodily implant 804 through a first implant engaging portion and a second anchor 802b is coupled to a second end portion 806b of the bodily implant 804 through a second implant engaging portion. The first anchor 806a defines a second axis extending from a distal end portion toward a proximal end portion of the first anchor 806*a*. The second axis for the first anchor 806*a* coincides with the longitudinal axis along the length of the first anchor 806*a*. Similarly, the anchor 806*b* also defines a second axis extending from a distal end portion toward a proximal end portion of the second anchor 806*b*. The second axis for the second anchor 806*b* coincides with the longitudinal axis along the length of the second anchor 806*b*.

The delivery tool 808 may be an elongated member such as a surgical needle that may be fitted to an anchor such as the anchor 806*a* and 806*b* during delivery of a bodily implant such as the bodily implant 804 as shown in FIG. 8A. The delivery tool 808 may include a shaft that may be substantially straight, curved or include both curved and straight portions. In some embodiments, a distal tip of the shaft is conically shaped to provide a sharp end facilitating insertion of the bodily implant 804 and the anchors 806*a* and 806*b* inside the body tissues.

At step 906, the medical device is inserted through the passageway in a patient's body. In some embodiments, the delivery tool 808 carrying the medical device is inserted through the vaginal incision that acts as the passageway for advancing the delivery tool 808. A force of insertion applied by the operator moves the medical device within the patient's body. Fingers of the operator may guide the delivery tool 808 inside the body to avoid blind delivery and hence, achieve effective advancement inside the body. The maximum depth of advancement through the vaginal incision must be limited to avoid perforation of the bladder wall.

In some embodiments, the anchors 802*a* and 802*b* of the medical device can be directly coupled to the delivery tool 808 for insertion into the body. The anchors 806*a* and 806*b* can include slots or interfaces disposed on their proximal end portions such that a distal tip portion or a needle tip of the delivery tool 808 can be engaged through the slots or interfaces of the anchors 806*a* and 806*b*. This provides a coupling of the delivery tool 808 with the anchors 806*a* and 806*b* such that an engagement of the anchors 806*a* and 806*b* with the delivery tool 808 through the slots or the interfaces ensure proper delivery and insertion of the medical device into the body tissues.

In accordance with some other embodiments, a delivery lead such as the delivery lead 302 may be utilized for inserting the medical device into the body. In some embodiments, the delivery lead 302 includes a loop that can be coupled to the delivery tool 808. The loop is configured to be hooked to the delivery tool such that the delivery lead 302 is pushed into the body, upon insertion of the delivery tool 808 through the vaginal incision, and comes out through groin area or abdomen of the patient. The delivery lead 302 can be finally unhooked from the tool 808 and the tool 808 is pulled out through the vaginal incision backward. In some embodiments, the delivery lead 302 is then pulled outside to leave the anchors 802*a* and 802*b* inside the body. In accordance with various other embodiments, several other types of bodily incisions and insertion mechanisms may be employed to insert the medical device inside the patient's body depending on the preference of an operator or a physician and the condition of the patient to be treated.

Once the medical device is inserted and placed within the body, the tension of the bodily implant 804 is adjusted at step 808. In some embodiments, the operator may adjust the tension of the bodily implant 804 by stretching it manually after placement at its targeted location. In other embodiments, the tension may be adjusted by a tension member such as a suture. Various other procedures of adjusting tension may be utilized without limitations.

After an appropriate tension is confirmed in the bodily implant 804, it is anchored within the body tissues at step 810 by exerting a force capable of rotating the anchors 802*a* and 80*b* such that the second axis of the anchors 802*a* and 80*b* forms an angle with the first axis with respect to the anchors 802*a* and 80*b*. The anchoring is done by using the two anchors 802*a* and 802*b* that are coupled at the two end portions 806*a* and 806*b* of the bodily implant 804 through their implant engaging portions. For example, the first end portion 806*a* of the bodily implant 804 is anchored in a first portion of the body tissues using the first anchor 802*a* and the second end portion 806*b* of the bodily implant 804 is anchored in a second portion of the body tissues using the second anchor 802*b*.

In some embodiments, the anchoring of the bodily implant 804 is done by first exerting a force on the bodily implant 804 outward at a portion that extends and hangs out of the patient's body. For example, a force may be exerted on the bodily implant 804 outward to anchor the first end portion 806*a* of the bodily implant 804 using the first anchor 802*a*. This causes the development of a pulling force that acts in a direction opposite to the direction of the insertion as a result of an interaction of the bodily implant 804 with the body tissues. Since the first end portion 806*a* of the bodily implant 804 is asymmetrically coupled on the lateral portion of the first anchor 802*a* within the implant engaging portion, the pulling force develops at the lateral portion of the first anchor 802*a* eccentrically and not to the centre.

Figure 10:
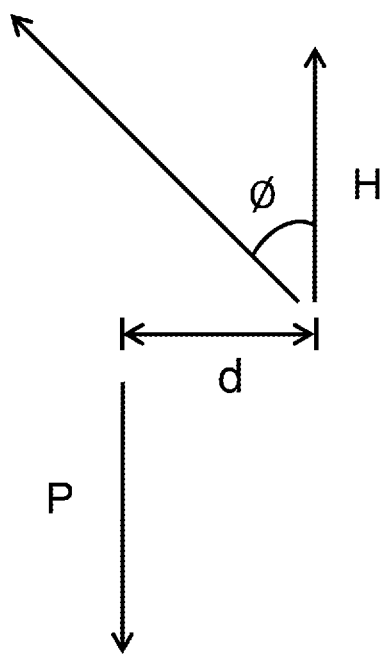
FIG. 10 is a schematic diagram illustrating the mechanics of the forces, in accordance with an embodiment of the present invention.

As a result of the development of the pulling force, a holding force starts developing at a catching point. The catching point is present on the bottom proximal right side of the anchor 802*a*. When the anchor 802*a* is placed inside the body and the implant is pulled down, the anchor 802*a* slightly goes down and hits the passageway at the catching point. This helps pivot the anchor 802*a* into a rotated configuration with respect to the passageway. The holding force at the catching point and the pulling force along the bodily implant 804 form a force couple or a turning momentum, which rotates the first anchor 802*a*. The rotation of the anchor 802*a* makes the distance between the forces of the turning momentum greater, thereby increasing the turning momentum even more. In this scenario, snow cone effect develops that tilts the anchor 802*a* by an angle formed between the first axis and the second axis. Therefore, the first anchor 802*a* is lodged within the tissues and creates a large holding force capable of restoring the anchor 802*a* at the desired position. The mechanics of the forces is illustrated in FIG. 10. As illustrated in the FIG. 10, 'P' represents the pulling force applied along the bodily implant 804, 'H' represents the holding force generated as a result of the pulling force, 'Ø' represents the angle formed between the first axis and the second axis after the first anchor 802*a* rotates, 'd' represents a distance between the lines of action of the two forces—the holding force and the pulling force.

The turning momentum at an engagement point of the implant engaging portion and the bodily implant 804 that causes rotation of the anchor 802*a* tries to bring it downward with respect to the body tissues. This changes the direction of the first anchor 802*a* and its proximal end portion now faces opposite to the lateral edge of the bodily implant 804 in a transverse direction, thereby engaging it with the body tissues at the catching point. The angle of rotation resulting from the effect of the turning momentum may be measured as an angle formed between the first axis defined by the passageway and the second axis defined by the longitudinal direction of the first anchor 802*a* joining the proximal and distal end portions of the first anchor 802a. The angle thus formed between the first axis and the second axis as a result of rotation is depicted in FIGS. 5 and 10 as Ø.

The anchoring of the first end portion 806a of the bodily implant 804 is achieved by rotating the anchor 802a on application of a pulling force on the bodily implant 804 as described above. In accordance with other embodiments, the turning momentum that is capable of rotating the first anchor 802a can be generated by pulling a second lead termed as a tilt control 402 as illustrated in FIG. 4 from its distal end. A proximal end of the tilt control lead 402 is coupled to the proximal end of the first anchor 802a in a manner as described in conjunction with FIG. 4. The operator may exert a force on the tilt control lead 402 to rotate the anchor 802a such that the second axis defined by the longitudinal direction of the first anchor 802a makes an angle Ø with the first axis defined by the passageway. In accordance with still other embodiments, a pulling force on the bodily implant 804 as well as a pulling force on the tilt control lead 402 can be applied together to achieve a desired angle Ø between the first axis and the second axis such that the anchor 802a is appropriately lodged in the body tissues.

In a manner similar to the anchoring of the first end portion 806a of the bodily implant 804 with the use of the first anchor 802a at the first implant engaging portion, the second end portion 806b of the bodily implant 804 may also be anchored using the second implant engaging portion of the second anchor 802b. The second implant engaging portion is coupled at the second end portion 806b of the bodily implant 804. In this scenario, an angle is formed between the first axis and the second axis with respect to the second anchor 802b. In some embodiments, the angle formed between the first axis and the second while anchoring the first anchor 802a is same as the angle formed between the first axis and the second while anchoring the second anchor 802b. In other embodiments, the angle formed between the first axis and the second while anchoring the first anchor 802a is different than the angle formed between the first axis and the second while anchoring the second anchor 802b. In accordance with various embodiments, the rotation angle Ø formed between the first axis and the second axis may vary based on the requirements such as the intended use and placement location of the bodily implant 804.

In accordance with various embodiments, re-positioning of the bodily implant 804 may be done in case the bodily implant 804 is found to be placed incorrectly. In order to reposition the bodily implant 804, the operator may exert a force on the delivery lead 302 coupled to the distal end portion of the anchor such as the anchor 802a and 802b. An appropriate force on the delivery lead 302 aligns the second axis with the first axis such that the longitudinal direction of the anchor such as the anchor 802a and 802b coincides with the direction of the passageway. Thus, the anchor such as the anchor 802a and 802b are no more in a rotated configuration. The operator adjusts the placement of the anchor (802a and 802a) and finally rotates them in accordance with various embodiments described above.

In some embodiments, the anchors 802a and 802b can be left to stay inside the body tissues. In some other embodiments, the anchors 802a and 802b can be removed from the patient's body. The anchors 802a and 802b can be removed by exerting a force on the tilt control lead such that the anchors 802a and 802b are rotated by 180 degree (with respect to the direction of the passageway) to align the first axis and the second axis. This makes the distal ends of the anchors 802a and 802b face toward the direction of the passageway such that a simple pull applied on the distal ends of the anchors 802a and 802b can remove them outside the patient's body. In some other embodiments, the anchors (802a and 802b) can be removed even without rotating through the 180 degree angle. In accordance with these embodiments, a simple pull is required at the delivery lead 302 or at the delivery lead 302 and the bodily implant 804 together to straighten the anchors (802a and 802b) such that the first axis coincides with the second axis. In this scenario, a pull of magnitude equivalent to rotate the anchors (802a and 802b) by an angle Ø and in opposite direction can straighten the anchors (802a and 802b). The anchors (802a and 802b) can be easily removed from the body by pulling them outside manually in a backward direction once they are in straight configuration.

The method for implanting and anchoring a bodily implant using anchors is described in conjunction with the bodily implant 804 and the anchors 802a and 802b above. However, the anchors such as 102 and 202 can also be used to anchor the bodily implant in accordance with various other embodiments of the present invention. Similarly, the bodily implant 104, 304, and various other kinds of bodily implants as used conventionally may also be employed.

In one embodiment, an anchor for anchoring a bodily implant within a body of a patient includes a distal end portion configured to pass through a passageway in the patient's body, the passageway defining a first axis and a proximal end portion disposed longitudinally opposite to the distal end portion on the anchor. The anchor defines a second axis extending from the distal end portion to the proximal end portion. A medial portion having an implant engaging portion for engaging the bodily implant, the implant engaging portion disposed on a lateral portion of the anchor. The anchor is configured to rotate such that the second axis defined by the anchor forms an angle with the first axis defined by the passageway upon rotation.

In some embodiments, the implant engaging portion includes at least one protuberance for engaging the bodily implant therewith. In some embodiments, the implant engaging portion includes a movable locking mechanism for engaging the bodily implant. In some embodiments, the implant engaging portion includes a slidable locking mechanism for engaging the bodily implant. In some embodiments, the implant engaging portion includes a first protuberance and a second protuberance configured to interlock with each other and engage the bodily implant therewithin.

In some embodiments, the proximal end portion defines an opening for coupling a tilt control lead with the anchor. In some embodiments, the anchor is configured to be rotated when a force is exerted on the tilt control lead. In some embodiments, the anchor is rotated to align the first axis and the second axis for removal of the anchor such that the distal end portion faces the passageway.

In some embodiments, the proximal end portion is substantially cylindrical. In some embodiments, the distal end portion is substantially conical. In some embodiments, the distal end portion defines an opening for engaging a delivery lead with the anchor. In some embodiments, the anchor is composed of at least one of a bio-compatible material, plastic, polypropylene, metal, ceramic, polymer, magnet, and alloy.

In some embodiments, a medical device is configured to be inserted within a body of a patient. The medical device includes a bodily implant and an anchor. The anchor includes a distal end portion configured to pass through a passageway in the patient's body, the passageway defining a first axis and a proximal end portion disposed longitudinally opposite to the distal end portion on the anchor. The anchor defines a second axis extending from the distal end portion to the proximal end portion and a medial portion having an implant engaging portion for engaging the bodily implant. The implant engaging portion disposed on a lateral portion of the anchor. The anchor is configured to rotate such that the second axis defined by the anchor forms an angle with the first axis defined by the passageway upon rotation.

In some embodiments, the implant engaging portion includes at least one protuberance for engaging the bodily implant therewith. In some embodiments, the implant engaging portion includes a movable locking mechanism for engaging the bodily implant. In some embodiments, the implant engaging portion includes a slidable locking mechanism for engaging the bodily implant. In some embodiments, the implant engaging portion includes a first protuberance and a second protuberance configured to interlock with each other and engage the bodily implant therewithin.

In some embodiments, the proximal end portion defines an opening for coupling a tilt control lead with the anchor. In some embodiments, the anchor is configured to be rotated when a force is exerted on the tilt control lead. In some embodiments, the anchor is rotated to align the first axis and the second axis for removal of the anchor and such that the distal end portion faces the passageway.

In some embodiments, the proximal end portion is substantially cylindrical. In some embodiments, the distal end portion is substantially conical. In some embodiments, the distal end portion defines an opening for engaging a delivery lead with the anchor. In some embodiments, the anchor is composed of at least one of a bio-compatible material, plastic, polypropylene, metal, ceramic, polymer, magnet, and alloy.

In some embodiments, the bodily implant is a mesh. In some embodiments, the bodily implant is composed of a bio-compatible material. In some embodiments, the bodily implant comprises at least one end portion, wherein the at least one end portion of the bodily implant is engaged with the anchor at the implant engaging portion.

In some embodiments, a method for anchoring a bodily implant within a body of a patient includes (1) inserting the bodily implant within the patient's body through a passageway, the passageway defining a first axis, an end portion of the bodily implant being coupled to a lateral portion of an anchor, the anchor defining a second axis extending from a distal end portion of the anchor to a proximal end portion of the anchor; and (2) exerting a force configured to rotate the anchor such that the second axis defined by the anchor forms an angle with the first axis defined by the passageway.

In some embodiments, the anchor is a first anchor and the end portion is a first end portion of the bodily implant. The method includes coupling a second end portion of the bodily implant to a second anchor at a lateral portion of the second anchor.

In some embodiments, the method includes inserting an elongated member into the patient's body to create the passageway therein. In some embodiments, the method includes exerting a force on a delivery lead coupled to the distal end portion of the anchor to align the second axis with the first axis. In some embodiments, the method includes exerting a force on a tilt control lead to rotate the anchor such that the second axis defined by the anchor is aligned with the first axis defined by the passageway.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. An anchor for anchoring a bodily implant within a body of a patient, the anchor comprising:
 a distal end portion configured to pass through a passageway in the patient's body, the distal end portion having a lumen defined therethrough, the passageway defining a first axis;
 a removable delivery lead extending through the lumen, the delivery lead configured to facilitate insertion of the anchor in the passageway;
 a proximal end portion disposed longitudinally opposite to the distal end portion on the anchor, the proximal end portion including a tilt control lead,
 wherein the anchor defines a second axis extending from the distal end portion to the proximal end portion, the second axis being substantially parallel with the first axis defined by the passageway when the anchor is inserted in the passageway; and
 a medial portion having an implant engaging portion for engaging the bodily implant, the implant engaging portion disposed on a lateral portion of the anchor, the implant engaging portion including a first protuberance and a second protuberance configured to engage the bodily implant, at least one of the first protuberance and the second protuberance being movable relative to a body of the anchor so as to engage the bodily implant,
 the tilt control lead extending from the proximal end portion, the tilt control lead being configured to facilitate rotation of the anchor in the passageway such that the second axis defined by the anchor is non-parallel with the first axis defined by the passageway to help secure the anchor in the passageway.

2. The anchor of claim 1, wherein at least one of the first protuberance and the second protuberance includes a movable locking mechanism for engaging the bodily implant.

3. The anchor of claim 1, wherein at least one of the first protuberance and the second protuberance includes a slidable locking mechanism for engaging the bodily implant.

4. The anchor of claim 1, wherein the first protuberance and the second protuberance are configured to interlock with each other.

5. The anchor of claim 1, wherein the proximal end portion defines an opening for coupling the tilt control lead with the anchor.

6. The anchor of claim 5, wherein the anchor is configured to be rotated when a force is exerted on the tilt control lead.

7. The anchor of claim 1, wherein the anchor is rotated to align the first axis and the second axis for removal of the anchor such that the distal end portion faces the passageway.

8. The anchor of claim 1, wherein the proximal end portion is substantially cylindrical.

9. The anchor of claim 1, wherein the distal end portion is substantially conical.

10. The anchor of claim 1, wherein the anchor is composed of at least one of a bio-compatible material, plastic, polypropylene, metal, ceramic, polymer, magnet, and alloy.

11. A medical device configured to be inserted within a body of a patient, the medical device comprising:
 a bodily implant;
 an anchor including:
 a distal end portion configured to pass through a passageway in the patient's body, the passageway defining a first axis;
 a proximal end portion disposed longitudinally opposite to the distal end portion of the anchor, the anchor defining a second axis extending from the distal end portion to the proximal end portion;

a medial portion having an implant engaging portion for engaging the bodily implant, the implant engaging portion disposed on a lateral portion of the anchor; and a lumen formed through the proximal portion; and a tilt control lead extending proximally from the lumen, wherein the tilt control lead, when manipulated by an operator, rotates the anchor from the proximal end portion such that the second axis defined by the anchor forms a non-zero angle with the first axis defined by the passageway to help secure the anchor in the passageway; and a delivery lead extending from the distal end portion, the delivery lead configured to be removeably coupled with the anchor and facilitate insertion of the anchor in the passageway.

12. The medical device of claim 11, wherein the implant engaging portion includes at least one protuberance for engaging the bodily implant therewith.

13. The medical device of claim 11, wherein the implant engaging portion includes a movable locking mechanism for engaging the bodily implant.

14. The medical device of claim 11, wherein the implant engaging portion includes a slidable locking mechanism for engaging the bodily implant.

15. The medical device of claim 11, wherein the implant engaging portion includes a first protuberance and a second protuberance configured to interlock with each other and engage the bodily implant therewithin.

16. An anchor for anchoring a bodily implant within a body of a patient, the anchor comprising:

a distal end portion configured to pass through a passageway in the patient's body, the passageway defining a first axis, the distal end portion having a lumen formed therethrough;

a removable delivery lead extending through the lumen and away from the distal end portion, the delivery lead configured to facilitate insertion of the anchor in the passageway;

a proximal end portion disposed longitudinally opposite to the distal end portion on the anchor, wherein the anchor defines a second axis extending from the distal end portion to the proximal end portion;

a medial portion having an implant engaging portion for engaging the bodily implant, the implant engaging portion disposed on a lateral portion of the anchor and including at least one protuberance for engaging the bodily implant therewith, the at least one protuberance being aligned along the second axis, the implant engaging portion further including a movable locking mechanism for engaging the bodily implant; and a tilt control lead extending from the proximal end portion, the tilt control lead being configured to facilitate rotation of the anchor such that the second axis defined by the anchor forms a non-zero angle with the first axis defined by the passageway to help secure the anchor in the passageway.

17. The anchor of claim 16, wherein the at least one protuberance includes a first protuberance and a second protuberance configured to interlock with each other and engage the bodily implant.

18. The anchor of claim 16, wherein the proximal end portion defines an opening for coupling the tilt control lead with the anchor.

19. The anchor of claim 16, wherein the anchor is configured to be rotated when a force is exerted on the tilt control lead.

* * * * *